United States Patent
Garris

(10) Patent No.: US 8,158,144 B2
(45) Date of Patent: Apr. 17, 2012

(54) HAIR CARE SOLUTION PROTECTING NATURAL HAIR FROM GLUING PRODUCTS

(76) Inventor: Calvin Garris, Greenville, NC (US)

( * ) Notice: Subject to any disclaimer, the term of this patent is extended or adjusted under 35 U.S.C. 154(b) by 459 days.

(21) Appl. No.: 11/897,068

(22) Filed: Oct. 18, 2007

(65) Prior Publication Data

US 2008/0260872 A1 Oct. 23, 2008

Related U.S. Application Data

(60) Provisional application No. 60/844,709, filed on Sep. 15, 2006.

(51) Int. Cl.
*A61K 9/00* (2006.01)
(52) U.S. Cl. .......................................... 424/440
(58) Field of Classification Search .................. None
See application file for complete search history.

(56) References Cited

U.S. PATENT DOCUMENTS

| | | | | | |
|---|---|---|---|---|---|
| 3,960,782 | A | * | 6/1976 | Daley et al. .................. | 510/128 |
| 5,747,022 | A | | 5/1998 | Slavtcheff | |
| 6,043,202 | A | * | 3/2000 | Eriksen et al. ............... | 510/119 |
| 7,837,742 | B2 | | 11/2010 | Morrissey et al. | |
| 2003/0086954 | A1 | | 5/2003 | O'Halloran et al. | |
| 2003/0228272 | A1 | * | 12/2003 | Amjad et al. ............... | 424/70.28 |
| 2004/0161402 | A1 | | 8/2004 | Brooks et al. | |
| 2004/0161435 | A1 | | 8/2004 | Gupta | |
| 2005/0019291 | A1 | | 1/2005 | Zolotarsky et al. | |
| 2007/0031360 | A1 | | 2/2007 | Gupta | |
| 2007/0258935 | A1 | | 11/2007 | McEntire et al. | |
| 2008/0260872 | A1 | | 10/2008 | Garris | |

FOREIGN PATENT DOCUMENTS

| | | |
|---|---|---|
| JP | 59062512 | 4/1984 |
| JP | 62093210 | 4/1987 |
| JP | 63057508 | 3/1988 |
| JP | 63057509 | 3/1988 |
| JP | 05238914 | 9/1993 |
| JP | 08081349 | 3/1996 |
| JP | 08245340 | 9/1996 |
| JP | 2000086440 | 3/2000 |
| JP | 2002226354 | 8/2002 |
| WO | 0124770 | 4/2001 |
| WO | WO 0130882 A1 * | 5/2001 |

OTHER PUBLICATIONS

Mottram et al. "9 Hair Shampoos". Publication Date: 2000 [Retrieved from the Internet on: Oct. 11, 2011]. Retrieved from the Internet: <URL: http://www.monzir-pal.net/Industrial/Shampoo.pdf>.*

"Dowicil 200 Preservative". Publication date: 1999 [Retrieved from the Internet on: Oct. 11, 2011]. Retrieved from the Internet: <URL: http://msdssearch.dow.com/PublishedLiteratureDOWCOM/dh_0309/0901b80380309e04.pdf?filepath=biocides/pdfs/noreg/253-01176.pdf&fromPage=GetDoc>.*
"The herbarie polyquaternium 7". Internet Archive Date: May 7, 2006 [Retrieved from the Internet on: Oct. 11, 2011]. Retrieved from the Internet: <URL: http://web.archive.org/web/20060507232333/http://theherbarie.com/Polyquaternium-7-pr-53.html>.*
"Smart Skin care.com" . Internet Archive Date: Aug. 5, 2004 [Retrieved from the Internet on: Oct. 11, 2011]. Retrieved from the Internet: <URL: http://web.archive.org/web/20040805114219/http://www.smartskincare.com/ingredients/glossary/ingredients_a.html>.*
http://van.physics.illinois.edu/qa/listing.php?id=1743; "Ask the Van—Deionized Water", 2010.
Chemical and Technical Assessment, 61st JECFA, "Polyvinyl Alcohol (PVA)", Chemical and Technical Assessment (CTA), by S.K. Saxena, 2004.
http://www.dermadoctor.com/article_Cosmetic-Ingredients_108.html; "Cosmetic Ingredients" web article, Audrey Kunin, MD, 2010.
http://www.inchem.org/documents/icsc/icsc/eics1517.htm, Chemical Product Bulletin entitled "Polyethylene Glycol 200-ICSC1517", copyright 1999.
CTFA International Cosmetic Ingredient Dictionary, Fourth Edition, 1991, p. 462 and 509.
NALCO, Inc., "Product Bulletin PC-PolyQ-7", 2007, p. 1.
http://www.cosmeticingredients.co.uk/products.asp?prod=271, Adina Inc, "Adina Cosmetic Ingredients", 2009.
http://www.merriam-webster.com/dictionary/botanical?show=1&t=1290220361, Merriam-Webster's Online Dictionary, definition of "Botanical", Nov. 19, 2010.
http://en.wikipedia.org/wiki/Aloe_barbadensis, Nov. 19, 2010.
http://en.wikipedia.org/wiki/Tea_tree_oil, Nov. 19, 2010.
http://en.wikipedia.org/wiki/Anthemis_nobilis, Nov. 19, 2010.
"DOWICIL 200 Preservative", Dow Chemicals Inc., Product Brochure for Dowicil 200, May 1999.
"Morning Glory Gro-Protest Solutions a Crystallizing Protective Growth Serum Ice Clear" http://www.hairwigbeautysupply.com/servlet/the-17194/morningglory-gro-protest/Detail (Accessed Jan. 28, 2011).

* cited by examiner

Primary Examiner — Amy L Clark

(57) ABSTRACT

The hair gluing product of the invention is a clear gel or crystallizing protective growth serum that dries down to form a peelable film over your natural hair and scalp. The invention allows for application of hair bonding glue without damaging natural hair or scalp. It contains aloe extract, tea tree oil, chamomile extract. It is available in an assortment of colors. The purpose of the gel or serum is to protect client's natural hair/scalp from being damaged by the use of hair bonding glue, which is used for weaving styles. When hair bonding glue is applied directly to the natural hair and scalp it has a tendency to cause breakage and leads to damage hair the invention will cover the natural hair and scalp, which will allow the hair bonding glue to be applied directly to the shield that appears after the invention dries on the hair/scalp.

2 Claims, No Drawings

HAIR CARE SOLUTION PROTECTING NATURAL HAIR FROM GLUING PRODUCTS

CROSS REFERENCE TO RELATED APPLICATIONS

This application claims benefit of earlier filed U.S. Provisional Application No. 60/844,709 filed Sep. 15, 2006, which is incorporated herein by reference.

FIELD OF THE INVENTION

The purpose of the instant invention is to protect natural hair/scalp from being damaged by the use of hair bonding glue, which is used for weaving styles.

BACKGROUND OF THE INVENTION

Hair bonding glue is used for weaving styles. When hair bonding glue is applied directly to the natural hair and scalp it has a tendency to cause breakage and leads to damaged hair.

There exists a need for crystallizing protective growth serum that provides protection from gluing products while stimulating growth to your natural hair and protecting client's natural hair/scalp from being damaged by the use of hair bonding glue.

SUMMARY OF THE INVENTION

An object of the invention is to provide a solution for hair protection from bonding glue.

A further object is keeping your natural hair healthy while wearing all the fun styles you desire.

A still further object is a conditioning protection system providing professional long lasting results that keeps your natural hair and skin healthy until your next hair care service.

Yet another object is a crystallizing protective growth serum, which has been designed to protect the hair from gluing products.

A further object is hair protection from gluing products, which are known as bonding glue.

Yet a further object is a crystallizing protective growth serum that provides protection from gluing products while stimulating growth of natural hair.

Yet a further object is to provide a gel or serum that contains tea tree oil, leaf oil, chamomile flower extract, aloe babadenesis, aloe vera leaf extract, and a pleasant fragrance.

DETAILED DESCRIPTION OF THE INVENTION

The instant invention is a clear gel that dries down to form a peelable film over your natural hair and scalp. The instant invention allows for application of hair bonding glue without damaging natural hair or scalp. Contains aloe extract, tea tree oil, chamomile extract. The instant invention will be available in an assortment of colors.

The invention protects client's natural hair/scalp from being damaged by the use of hair bonding glue, which is used for weaving styles. When hair bonding glue is applied directly to the natural hair and scalp it has a tendency to cause breakage and leads to damaged hair.

The invention will cover the natural hair, which will allow the hair bonding glue to be applied directly to the shield that appears after the invention dries on the hair/scalp.

The instant invention is a crystallizing protective growth serum, which has been designed to protect the hair from gluing products. The instant invention provides hair protection from gluing products. The instant invention is better technology for healthier hair, keeping your natural hair healthy while wearing all the fun styles you desire. How do I keep bonding glue from causing damage? The instant invention formula is a conditioning protection system that provides professional long lasting results that keep you natural hair and skin healthy until you next hair care service. The instant invention is a crystallizing protective growth serum that provides protection from gluing products, while stimulating hair growth to your natural hair. Ingredients tea tree oil, leaf oil, chamomile flower extract, aloe babadnesis, aloe vera leaf extract along with a pleasant fragrance.

A first exemplary solution provides a brown hair gluing product formulation, product number HCB-022CB:
- 55% de-ionized water (water DI),
- 10% Polyvinyl Alcohol (PVA),
- 18% denatured alcohol (Alcohol SDA-40),
- 5% Poly Ethylene Glycol 200 molecular weight (PEG-200),
- 1% Polyquaternium 7 (MERQUAT 550),
- 10% Arianor Sienna Brown (1% solution) (commercially available colorant)
- 0.01% Tea Tree leaf oil,
- 0.15% Chamomile Flower Extract,
- 0.15% Aloe Vera Extract.
- 0.59% of a fragrance and
- 0.10% of Quaternium 15 (Dowicil 200).

A second exemplary solution provides a black hair gluing product formulation, product number HCB-022CE:
- 55% de-ionized water (water DI),
- 10% Polyvinyl Alcohol (PVA),
- 18% denatured alcohol (Alcohol SDA-40),
- 5% Poly Ethylene Glycol 200 molecular weight (PEG-200),
- 1% Polyquaternium 7 (MERQUAT 550),
- 10% Arianor Ebony Black (1.0% solution) (commercially available colorant).
- 0.01% Tea Tree leaf oil,
- 0.15% Chamomile Flower Extract,
- 0.15% Aloe Vera Extract.
- 0.59% of a fragrance and
- 0.10% of Quaternium 15 (Dowicil 200).

A third exemplary solution provides a clear hair gluing product formulation, product number HCB-022C:
- 65% de-ionized water (water DI),
- 10% Polyvinyl Alcohol (PVA),
- 18% denatured alcohol (Alcohol SDA-40),
- 5% Poly Ethylene Glycol 200 molecular weight (PEG-200),
- 1% Polyquaternium 7 (MERQUAT 550),
- 0.01% Tea Tree leaf oil,
- 0.15% Chamomile Flower Extract,
- 0.15% Aloe Vera Extract.
- 0.59% of a fragrance and
- 0.10% of Quaternium 15 (Dowicil 200).

The hair gluing product manufacturing directions:
1. Add water and Poly Ethylene Glycol 200 molecular weight (PEG-200) to the batch tank.
2. Heat to 70 C. with stirring
3. Sift in Polyvinyl Alcohol (PVA) slowly.
4. Remove heat and continue to stir until clear.
5. Cool the batch to below 40 C.
6. Add denatured alcohol (Alcohol SDA-40) with stirring.
7. Allow to stand until clear.

8. Add Tea Tree oil, Chamomile extract, Aloe Vera extract, Polyquaternium 7 (MERQUAT 550).
9. Stir in fragrance and Quaternium 15 (Dowicil 200).
10. Stir in color if required.

The manufacturing directions produce the instant invention which includes a clear gel that dries down to form a peelable film over your natural hair and scalp and a crystallizing protective growth serum, which has been designed to protect the hair from gluing products. The instant invention allows for application of hair bonding glue without damaging natural hair or scalp. The invention protects client's natural hair/scalp from being damaged by the use of hair bonding glue, which is used for weaving styles. When hair bonding glue is applied directly to the natural hair and scalp it has a tendency to cause breakage and leads to damaged hair. The invention will cover the natural hair, which will allow the hair bonding glue to be applied directly to the shield that appears after the invention dries on the hair/scalp.

The invention claimed is:

1. A gel hair care product that dries down to form a peelable film over natural hair and scalp consisting of:
    55% de-ionized water, 10% Polyvinyl Alcohol, 18% denatured alcohol, 5% polyethylene glycol 200 molecular weight, 1% polyquaternium-7, 10% colorant in a 1% solution, 0.01% Tea Tree leaf oil, 0.15% Chamomile Extract, 0.15% Aloe Vera Extract, 0.59% of a fragrance and 0.10% quaternium-15.

2. A clear gel hair care product that dries down to form a peelable film over natural hair and scalp consisting of:
    65% de-ionized water, 10% Polyvinyl Alcohol, 18% denatured alcohol, 5% polyethylene glycol 200 molecular weight, 1% polyquaternium-7, 0.01% Tea Tree leaf oil, 0.15% Chamomile Extract, 0.15% Aloe Vera Extract, 0.59% of a fragrance and 0.10% quaternium-15.

* * * * *